US008897414B2

(12) United States Patent
Bernard et al.

(10) Patent No.: US 8,897,414 B2
(45) Date of Patent: Nov. 25, 2014

(54) METHOD, SYSTEM AND COMPUTER PROGRAM PRODUCT TO PROCESS A SET OF TOMOSYNTHESIS SLICES

(75) Inventors: Sylvain Bernard, Montigny le Bretonneux (FR); Henri Souchay, Versailles (FR)

(73) Assignee: General Electric Company, Schenectady, NY (US)

(*) Notice: Subject to any disclaimer, the term of this patent is extended or adjusted under 35 U.S.C. 154(b) by 908 days.

(21) Appl. No.: 12/783,584

(22) Filed: May 20, 2010

(65) Prior Publication Data
US 2010/0303325 A1    Dec. 2, 2010

(30) Foreign Application Priority Data
Jun. 2, 2009 (FR) ...................... 09 53635

(51) Int. Cl.
A61B 6/03 (2006.01)
A61B 6/00 (2006.01)
A61B 6/02 (2006.01)
G06T 11/00 (2006.01)

(52) U.S. Cl.
CPC .............. *G06T 11/006* (2013.01); *A61B 6/469* (2013.01); *A61B 6/025* (2013.01); *G06T 2211/436* (2013.01); *A61B 6/502* (2013.01); *A61B 6/463* (2013.01)
USPC ............... 378/23; 378/21; 715/772; 345/428; 345/629; 382/131; 703/11; 600/407; 600/425; 600/426

(58) Field of Classification Search
CPC .... A61B 6/463; A61B 6/469; G06T 221/436; G06T 11/006
USPC ............... 378/21, 23; 345/428, 629; 382/131; 703/11; 600/407, 425, 426; 715/772
See application file for complete search history.

(56) References Cited

U.S. PATENT DOCUMENTS

| 2006/0098855 A1 | 5/2006 | Gkanatsios et al. |
| 2007/0183564 A1 | 8/2007 | Li et al. |
| 2008/0101536 A1* | 5/2008 | Sendai ............................ 378/22 |
| 2008/0155451 A1* | 6/2008 | Lundstrom et al. ........... 715/772 |
| 2008/0219567 A1* | 9/2008 | Claus et al. ................... 382/232 |

FOREIGN PATENT DOCUMENTS

| DE | 10345073 A1 | 5/2005 |
| DE | 102007003714 A1 | 8/2007 |
| EP | 1792569 A2 | 6/2007 |

* cited by examiner

*Primary Examiner* — Mark Holcomb
*Assistant Examiner* — Jason Tiedeman
(74) *Attorney, Agent, or Firm* — GE Global Patent Operation; Marc A. Vivenzio

(57) ABSTRACT

Method to process a set of tomosynthesis slices, comprising; acquiring images of an object of interest using a detector of a machine also comprising an X-ray emitter; reconstructing a set of tomosynthesis slices of the object using a calculator, in relation to the acquired images; displaying slices on a display monitor with a first display increment; selecting a region of interest in a slice of interest; and using a second display increment that is finer than the first display increment to display on the display monitor regions of interest belonging to slices in the set, the regions of interest corresponding to the selected region of interest.

9 Claims, 7 Drawing Sheets

METHOD, SYSTEM AND COMPUTER PROGRAM PRODUCT TO PROCESS A SET OF TOMOSYNTHESIS SLICES

CROSS-REFERENCE TO RELATED APPLICATIONS

This application claims priority under 35 U.S.C. §119(a)-(d) or (f) to prior-filed, co-pending French patent application serial number 0953635, filed on Jun. 2, 2009, which is hereby incorporated by reference in its entirety.

BACKGROUND OF THE INVENTION

1. Field of Invention

The present invention relates to a method and system to process a set of tomosynthesis slices, and to a computer program product to implement the method.

It applies in particular, but is not limited to, a 3D radiography imaging technique called DBT ("Digital Breast Tomosynthesis"), or to so-called conventional 2D radiography of the breast or other organs.

2. Description of the Prior Art

Tomosynthesis imaging is a known technique in three-dimensional imaging.

With reference to FIG. 1, an image acquisition machine for tomosynthesis generally comprises an X-ray emitter 12 and a detector 11.

An object of interest O, for which it is desired to reconstruct a three-dimensional volume in the form of a set of slices, is arranged in the vicinity of the detector 11, on a platform 16 parallel to the detector for example.

The emitter 12 can be placed at different positions, which allows X-rays to be emitted in the direction of the object of interest at several angles. The X-rays are detected by the detector 11 after passing through the object; several images in two dimensions are thereby acquired from several angles of projection.

The angles of emission are limited, for example to ±15° relative to the vertical to the object.

These images are then processed to obtain a set of slices representing a three-dimensional digital reconstruction of the object.

In this set of slices, a practitioner seeks to identify lesions, any sites of micro-calcification or opaqueness for example in a breast, or any nodules in the lungs which are potentially cancerous. The practitioner can also seek to identify a bone fracture e.g. of the hand or shoulder. These lesions and fractures which are visible using a radiography imaging technique can generally be termed as "radiological signs".

In the state of the art of breast cancer screening, the slices are generally separated by a thickness of around 1 mm for a mean total of around 50 to 70 slices to be examined by the practitioner.

The size of microcalcifications varies approximately between 100 µm and 1 mm. Owing to the limited emission angles, these microcalcifications artificially appear in elongate form in the digital reconstruction of the breast, along an axis perpendicular to the detector. On this account, slices separated by a thickness of 1 mm are generally sufficient for their detection.

The shape of a microcalcification, however, is much better revealed by a slice passing through the object itself rather than by its reconstruction artifact.

It is also known that the Contrast-to-Noise Ratio (CNR) of a spherical microcalcification is optimal when a slice passes through the centre of the microcalcification. When diagnosing, the practitioner will pay particular attention to the shape of microcalcifications, an irregular shape possibly being a sign of malignity.

It would therefore be of interest to increase the probability of obtaining slices passing through microcalcifications to allow the practitioner to characterize these calcifications more easily, for example by reducing the sampling interval of the digital reconstruction.

The space between the slices would then be narrower—for example 0.5 mm rather than 1 mm—and the number of slices in the set would be increased—for example doubled which is not without raising problems.

First, the practitioner would have more slices to analyze, which implies more time-consuming examination and increased fatigue through repetitive examinations, which may generate errors of inattention and, in extreme cases, a wrong examination result which is contrary to the targeted objective.

Additionally, the quantity of data to be stored would increase with the number of slices, which raises non-negligible problems of memory space.

SUMMARY OF THE INVENTION

One purpose of the invention is to propose a method and system to process a set of tomosynthesis slices which would allow an increase in the probability of obtaining slices passing through microcalcifications, whilst bypassing these difficulties.

The invention affords numerous advantages.

The invention allows better characterization of radiological signs compared with the prior art (preferably by increasing the number of slices) whilst allowing viewing of only the information that is necessary for such characterization (by initially displaying the slices with a first increment).

It also avoids congestion of the memory system of the invention.

BRIEF DESCRIPTION OF THE DRAWINGS

Other characteristics, purposes and advantages of the invention will arise from the following description which is purely illustrative and non-limiting, and is to be read with reference to the appended drawings in which.

In all the figures, similar parts carry identical reference numbers.

DETAILED DESCRIPTION OF THE INVENTION

Figure 1:
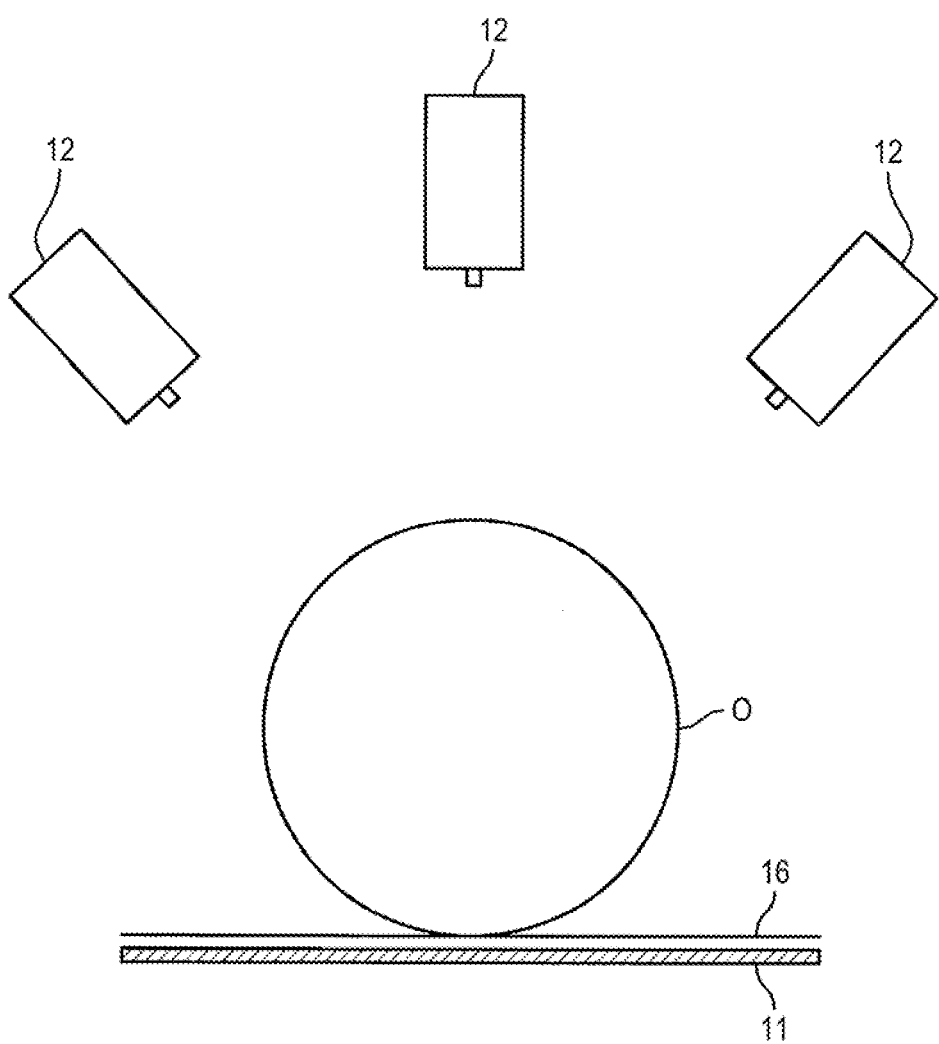
FIG. 1, already commented upon, shows a prior art image acquisition machine for tomosynthesis.
Figure 2:
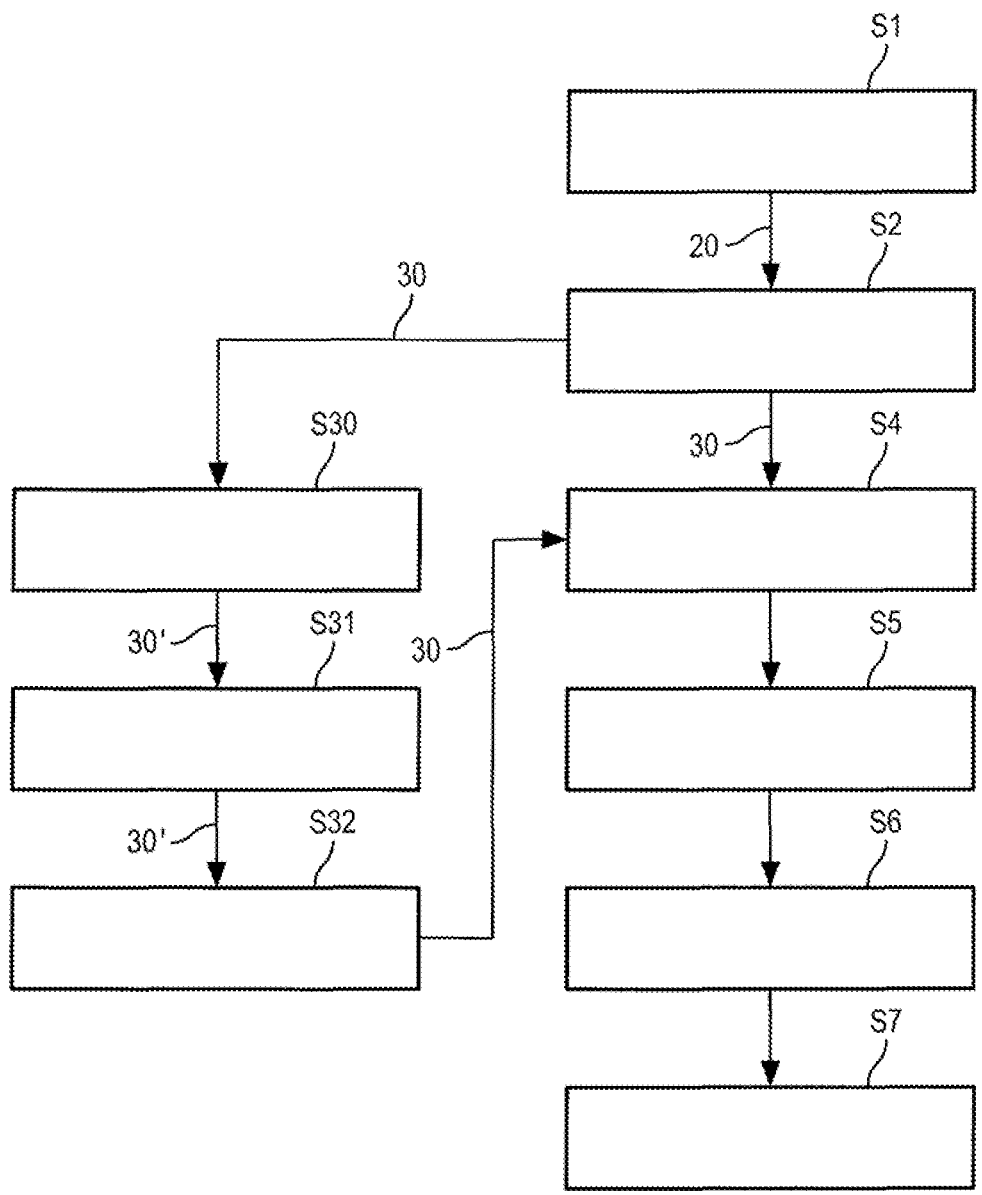
FIG. 2 is a block diagram of a method to treat a set of tomosynthesis slices according to one possible embodiment of the invention.
Figure 3:
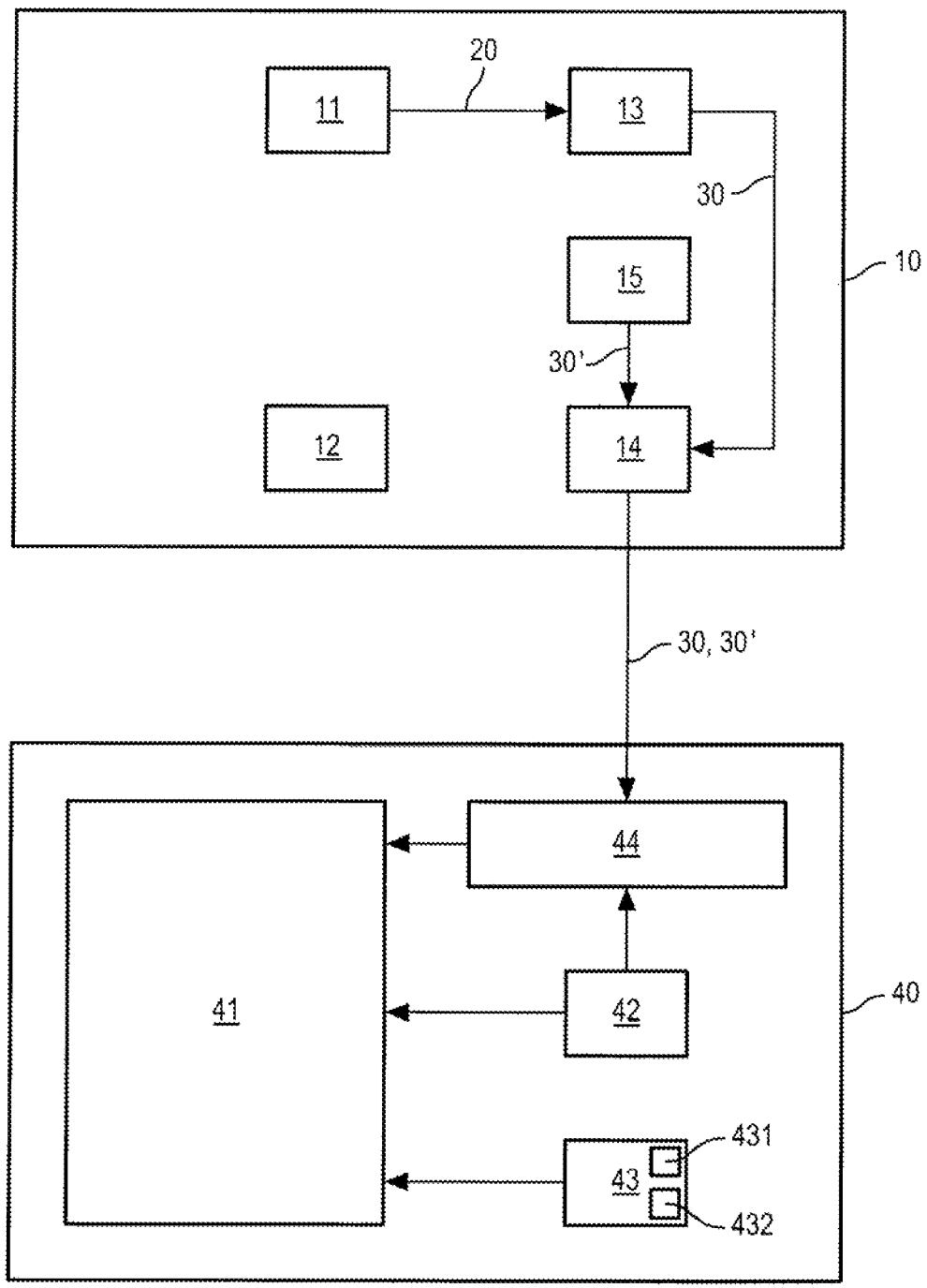
FIG. 3 schematically illustrates a system to treat a set of tomosynthesis slices according to one possible embodiment of the invention, cooperating with an image acquisition and slice reconstruction machine.

With reference to FIG. 2, and having regard also to FIG. 3, a method to process a set of tomosynthesis slices according to the invention chiefly comprises an acquisition step S1 of images 20 of an object of interest (a breast for example, but not limited thereto) by a detector 11 of a machine 10 also comprising an X-ray emitter 12, and a reconstruction step S2 of a set 30 of slices by a calculator 13, preferably included in the machine 10.

The reconstruction of slices by the calculator is known to persons skilled in the art and will not be described in further detail in the present description.

For one same object, the number of slices is preferably greater than in prior art tomosynthesis, and depends upon desired precision of analysis.

Figure 4:
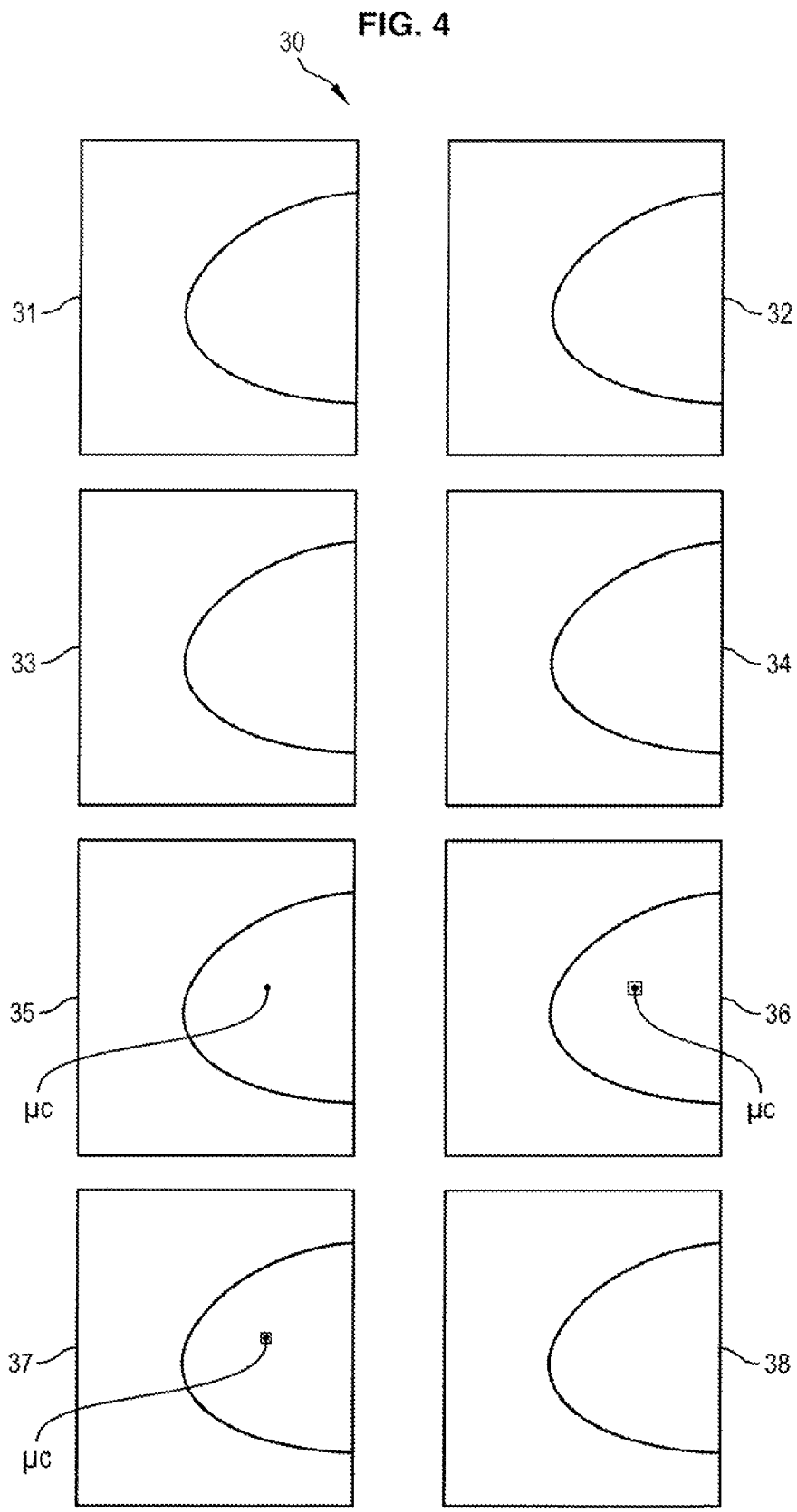
FIG. 4 shows a reduced set of tomosynthesis slices, some slices showing a microcalcification.

FIG. 4 shows a reduced set 30 of 8 tomosynthesis slices 31 to 38 of a breast, according to one possible embodiment of the invention. In this example, the slices 31 to 38 are separated two by two over a thickness of 0.5 mm. Evidently this set is reduced for illustration purposes and a set in fact comprises many more than 8 slices (around 140 slices for example).

For example, a set obtained conventionally contains around 70 slices. According to the invention 140 slices for example are reconstructed, or even more, the probability of obtaining relevant slices for the characterization of microcalcifications being increased accordingly.

The method of the invention further comprises a display step S4 to display slices of the set 30 on a display monitor 41 in a first display increment.

The monitor 41 is advantageously included in a system 40 according to the invention, the system further comprising a processor 42 to manage the display of slices on the monitor 41.

Preferably, but not limited thereto, prior to display the set is stored in a memory 44 of the system 40 according to the invention.

The machine 10 and the system 40 of the invention can be included in a common structure, or can be separated from each other as shown on FIG. 3. In this latter case, they can for example be located in one same examination room or geographically separated on different sites.

This allows the user practitioner to carry out an examination of tomosynthesis slices separately from acquisition and/or reconstruction.

The machine 10 then preferably comprises means 14 to transfer the set of slices towards the system 40, preferably towards the memory 44. The means 14 can be any conventional transfer means e.g. physical data storage medium (disc or storage peripheral), wire or wireless computer network.

It is to be noted that, once the slices have been transferred to the system 40, the images 20 can be deleted from the machine 10 and a new acquisition can be started.

Advantageously, the first display increment can be default set in the processor and can correspond to the display of one slice out of every N of the set, N being an integer.

N is preferably chosen so that the display of the set is sufficient to detect the lesions i.e. for microcalcifications the display of slices separated two by two by a thickness of 1 mm for example.

For example, if a set of slices is reconstructed using a separation thickness of 0.5 mm instead of 1 mm (140 slices instead of 70), the setting will be N=2 and it will be chosen to display every other slice by default.

Figure 5:
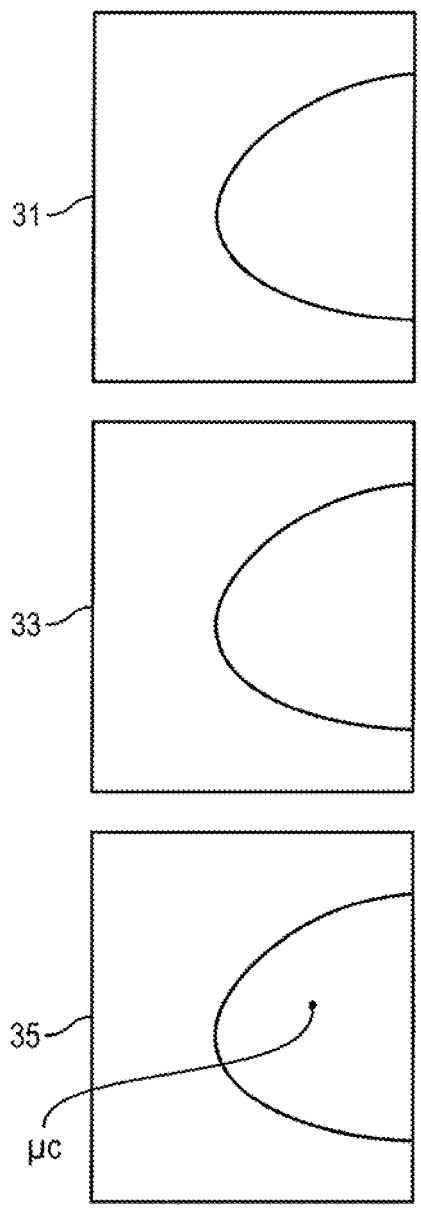
FIG. 5 shows three slices in the reduced set in their order of display and displayed with a first display increment, according to a possible embodiment of the invention.

FIG. 5 illustrates the display S4 using a first increment—every other slice—of the reduced set comprising slices 31, 33 and 35. Slices 32 and 34, although available in the memory 44, are not displayed.

Additionally, the method of the invention comprises a selection step S5, using selection means 43 of the system 40, to select a slice of interest or region of interest ROI in a slice of interest.

By "slice of interest" is meant a slice having a radiological sign of potential interest—e.g. a microcalcification—and by "region of interest" is meant a region in the displayed slice which includes this radiological sign.

For example, the region of interest may be a rectangle, a circle, or any other delimited region around the radiological sign.

Advantageously, the region of interest may also be the entirety of the slice of interest. In this case, the display S6 according to the second increment concerns full slices of the set.

Figure 6:
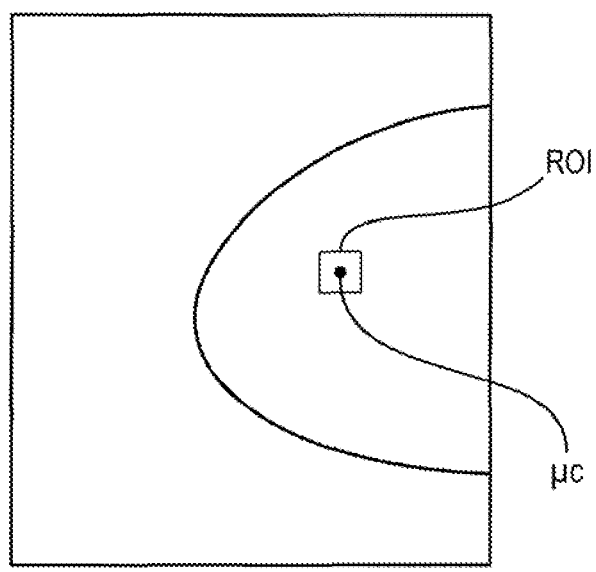
FIG. 6 shows a slice of interest in the reduced set having a region of interest, according to a possible embodiment of the invention.

Still with reference to the reduced set 30, FIG. 6 illustrates slice 35 which has a microcalcification μc with a ROI of rectangular shape.

After the ROI has been selected in the slice of interest 35, the processor 42 triggers display S6 in a second display increment which is finer than the first display increment, to display regions of slices in the set corresponding to the selected ROI in the slice of interest.

Preferably, the second display increment corresponds to the display at least in part of the whole set of consecutive slices. In this case slices 35, 36, 37 and 38 are displayed, as shown FIG. 7.

According to one possible embodiment of the invention, the selection means 43 comprise an interaction device 431 with a user practitioner, so that the practitioner himself/herself is able to select the ROI in the slice of interest and to initiate transition by the processor 42 from the first coarse display increment (e.g. display of every other slice) to the second display increment which is finer (all consecutive slices in the set, at least in part).

It is possible, but not limited thereto, that the device 431 may be a computer mouse for example, or keyboard or wheel of "jog" type, a small keyboard of keypad type, or part of the monitor 41 may be provided with touch detection. Any combination of these examples can be used. For example, by pressing on a key of the keyboard, this may trigger the display of whole slices of the set in the second display increment, whilst the mouse may be used to select the region of interest.

According to one variant of this possible embodiment of the invention, the selection step S5 to select a ROI may be performed manually i.e. by triggering a function dedicated to selection by actuating device 431.

According to another variant of this possible embodiment of the invention, the selection step S5 is performed semi-automatically i.e. by triggering a function having two effects, the second effect being triggering of display of slices in the set using the second display increment. This function may, for example, consist of zooming in on part of the slice of interest, of which the first effect is magnified display of a region.

According to another possible embodiment of the invention, the selection means 43 comprise an automatic detector 432 able to recognize radiological signs in the slices, and intended to select ROIs e.g. a visual recognition device of CAD type (Computer Aided Detection) known to those skilled in the art.

The selection step S5 of a ROI is then advantageously determined automatically i.e. without any action on the user's part, by the automatic detector 432.

According to another possible embodiment of the invention, the means 43 comprise firstly an interaction device 431, and secondly an automatic detector 432 known to persons skilled in the art.

The practitioner is therefore assisted in analysis by the detector 432, which reduces risks of examining errors.

For example, the detector 432 can perform a first detection on all the slices and, in relation to the image analysis method, can determine regions of interest around radiological signs. The changeover from one display increment to the other when viewing can then advantageously be made automatically.

In addition, the detector 432 may draw the attention of the practitioner to a radiological sign he/she may have missed.

Advantageously, the slices displayed in the second display increment are contiguous to the slice of interest.

The practitioner therefore proceeds with conventional examination of a set of slices in the first display increment until he/she detects a radiological sign of interest on the display screen. He/she can then trigger consecutive display of the following slices (slices 35, 36, 37 and 38 in FIG. 7) or previous slices (slices 35, 34, 33 for example) in the second display increment for more precise analysis of the radiological sign.

Displays S4 and S6 can be scrolled automatically or manually, as is described further on in the examples.

Figure 7:
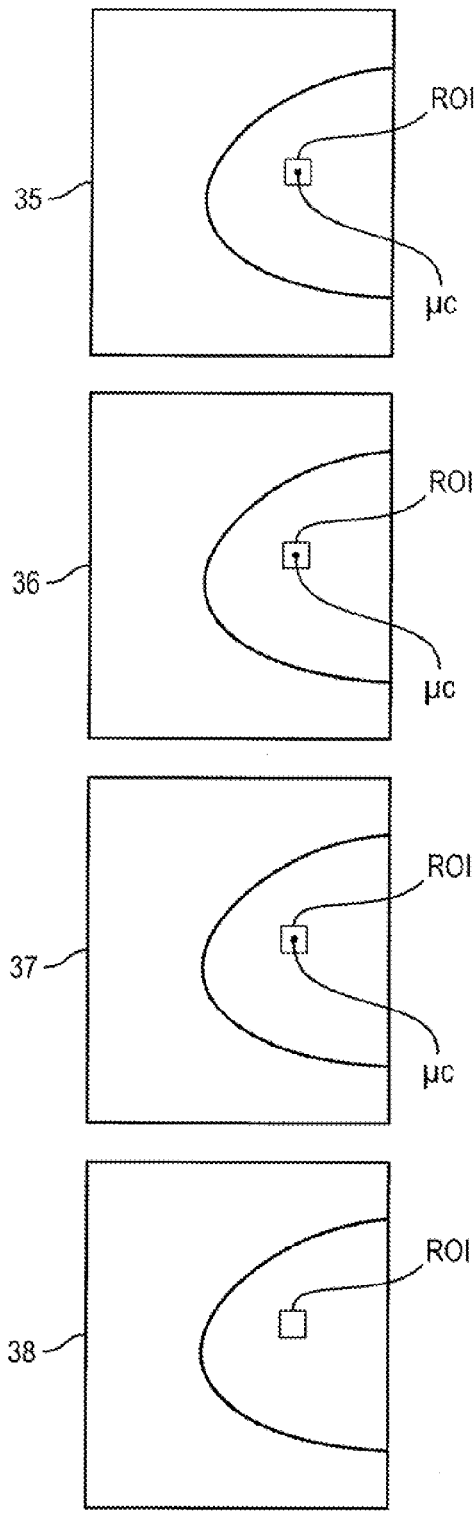
FIG. 7 shows four slices of the reduced set in their order of display and displayed with a second display increment, according to a possible embodiment of the invention.

With reference to FIG. 7, regions corresponding solely to the ROI selected in slice 35 (i.e. located at the same location in respective slices 36, 37, 38) are displayed.

Display according to the finer second increment allows better characterization of the radiological sign.

Advantageously, the method of the invention further comprises a return step S7 to display in the first increment. Therefore, after precise analysis of a radiological sign the practitioner can resume conventional examination from any slice in the set.

For example, slice 38 in FIG. 7 does not show any microcalcification. The practitioner can therefore choose to return to display of every other slice until a new radiological sign of interest is detected.

Preferably, the device 431 enables the practitioner to return to display in the first increment whenever wished, for example by a mouse click, by pressing on a key of the keyboard or by touching the screen 41.

Advantageously, the return to display in the first increment can be manual, semi-automatic or automatic.

The system of the invention therefore enables the practitioner to analyze regions of interest precisely whilst passing quickly over slices which do not show any radiological sign. The changeover from one display increment to the other is achieved simply by changing this increment automatically, semi-automatically or manually.

As shown FIG. 2, the method of the invention, after step S2, advantageously comprises a compression step S30 to compress at least part of the set of slices using a data compressor 15 which generates compressed data 30'.

The compressor 15 can implement any type of suitable image compression method. The compression method can be lossy or lossless as is known to those skilled in the art.

Preferably, the compression method makes use of the correlations between consecutive slices of the set 30.

The compressor 15 may be included in the machine 10 (as illustrated on FIG. 3) or in the system 40 of the invention. If the compressor 15 is included in the machine 10, one purpose of compression is to facilitate data transfer from the machine 10 towards the system 40.

The method of the invention advantageously comprises a decompression step S32 of data 30' by the processor 42 before step S4.

Decompression can also be carried out by a decompressor (not shown) separate from the processor.

If the compressor 15 is included in the machine 10, decompression S32 can be carried out before storage of the set 30 of slices in the memory 44. The method of the invention may comprise a storage step S31 of the compressed data 30' in the memory 44. In this case, decompression can be conducted at will just before display of a slice.

Advantageously, the memory 44 contains sufficient free space to store an entire decompressed set, which will allow rapid display of the slices in the set for the practitioner.

A description will now be given of some examples of implementation of the method according to the invention.

EXAMPLE 1

In this example, the displays S4 and S6 are both scrolled automatically at a scroll rate of one slice per second for example. Selection S5 is manual and is obtained on simple action by the user practitioner, such as pressing on a key of a keyboard or keypad if a slice of interest is displayed.

This simple action triggers display S6 of whole slices in the second display increment under automatic scrolling.

Return to display S4 for the first display increment is also manual, implemented by simple action made by the user practitioner.

In this example, the region of interest is the slice of interest in its entirety.

EXAMPLE 2

In this example, display S4 is automatically scrolled at a scroll rate of one slice per second for example, and display S6 is manually scrolled. Selection S5 is performed by the user manually.

Therefore, if a slice of interest is displayed during automatic scrolling, the user practitioner turns the computer mouse wheel, which triggers display S6 of whole slices in a second display increment.

The user practitioner scrolls the displayed slices in the second display increment manually by actuating the mouse wheel. The rate of scrolling depends upon the speed at which the wheel is turned.

Return to display S4 with the first display increment is manual.

In this example, the region of interest is the slice of interest in its entirety.

EXAMPLE 3

In this example, displays S4 and S6 are both scrolled automatically at a scroll rate of one slice per second for example. Selection S5 is semi-automatic.

Therefore, if a slice of interest with a radiological sign of interest is displayed, the user practitioner with a mouse click can trigger magnifying of a region of interest around the radiological sign of interest.

Magnification is obtained using a magnifying glass function known to those skilled in the art.

This mouse click also triggers display S6 of regions corresponding to the region of interest in contiguous slices of the set.

Return to display S4 is made semi-automatically by deactivating local magnification.

EXAMPLE 4

In this example, displays S4 and S6 are both automatically scrolled at a scroll rate of one slice per second for example. Selection S5 is semi-automatic.

Therefore, if a slice of interest with a radiological sign of interest is displayed, the user practitioner with a mouse click can trigger magnification of the entirety of the slice of interest.

Magnification is obtained using a zoom function known to those skilled in the art.

This mouse click also triggers display S6 of contiguous slices in the set in the second display increment.

Return to display S4 is made semi-automatically by deactivating the magnification.

In this example, the region of interest is the slice of interest in its entirety.

EXAMPLE 5 in this example, displays S4 and S6 are both manually scrolled. Selection S5 is semi-automatic.

The user practitioner triggers displays S4 and S6 by actuating a mouse wheel.

The display increment depends upon actuation of the mouse wheel. If the user practitioner turns the wheel continuously, the slices are displayed in the first display increment at a scroll rate which depends upon the speed at which the wheel is turned. If the user practitioner turns the wheel step by step the slices are displayed in the second display increment.

The user practitioner can therefore intuitively switch between displays S4 and S6.

According to one variant, display S6 can be triggered automatically if the turning of the wheel reaches a certain speed, for example if the scroll rate of display S4 exceeds the refresh rate of the display screen 41.

In this example, the region of interest is the slice of interest in its entirety.

EXAMPLE 6

Display S4 is automatically scrolled at a scroll rate of one slice per second for example, and display S6 is manually scrolled.

If a slice of interest with a radiological sign of interest is displayed, the user practitioner takes hold of a computer mouse and display S4 is stopped at the slice of interest.

Using the mouse, the user practitioner selects a region of interest of rectangular shape around the radiological sign.

The user practitioner then triggers display S6 of regions of slices in the set corresponding to the region of interest, by actuating the mouse wheel. The scrolling rate depends on the speed at which the wheel is turned.

EXAMPLE 7

In this example, displays S4 and S6 are both automatically scrolled at a scroll rate of one slice per second for example. Selection S5 is automatic and implemented by a detection device of CAD type.

Therefore, if the detection device detects a radiological sign of interest in a slice of interest, display S6 of regions of slices in the set is automatically triggered in all the slices containing the radiological sign.

The regions correspond to a region of interest determined automatically by the device of CAD type in the slice of interest.

The above examples are non-limiting. Any combination of automatic and manual scrolling can be envisaged for displays S4 and S6, and similarly selection S5 and the return to display S6 can each be carried out manually, semi-automatically or automatically.

An embodiment of a method performed in accordance with the principles of the invention is advantageously completed by the following characteristics, taken alone or in any technically possible combination:

the step to select a region of interest is made either manually by the user via an interaction device, or semi-automatically by the user via an interaction device, or automatically;

the display using a second display increment concerns the slices in the set contiguous to the slice of interest;

the method further comprises a return step to re-display slices in the set using the first display increment, made by a user either manually via an interaction device, or by a user semi-automatically via a device, or automatically;

the method further comprises the steps of compressing at least part of the set of slices using a data compressor which generates compressed data, and decompressing the compressed data, the compression step, for example, implementing a lossless or lossy compression method;

the first display increment corresponds to the display of one slice out of every N of the set, N being an integer preferably equal to 2;

the second display increment corresponds to the consecutive display of all the slices of at least part of the set.

For this purpose, the invention proposes a method to treat a set of tomosynthesis slices, comprising the steps of:

acquiring images of an object of interest using a detector of a machine also comprising an X-ray emitter;

reconstructing a set of tomosynthesis slices of the object, using a calculator, in relation to the acquired images;

displaying slices on a display screen, using a first display increment, selecting a region of interest in a slice of interest, and displaying on the display screen regions of slices in the set which correspond to the selected region of interest, using a second display increment finer than the first display increment.

The invention also concerns a system to process a set of tomosynthesis slices, characterized in that it comprises:

a display monitor, a processor to manage display of slices on the monitor, and means to select a region of interest in a slice of interest, the processor being intended to display slices in the set on the display monitor using a first display increment, and to use a second display increment finer than the first display increment (when a region of interest is selected by the selecting means) to display regions of slices in the set corresponding to the selected region of interest.

The system of the invention is advantageously completed by a data compressor and/or a memory.

The invention also proposes a computer program product comprising code instructions recorded on a computer-usable medium and instructions to implement the method of the invention.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of processing a set of tomosynthesis slices in a system including a machine coupled to a processor, the method comprising:
   acquiring image data of an object of interest using the machine, the machine comprising an X-ray emitter and a detector;
   reconstructing a set of individual tomosynthesis slices of the object from the acquired image data using a calculator; and
   using the processor to:
      display at least one slice out of every N slices of the reconstructed set of individual tomosynthesis slices on a display monitor, where N is an integer value of at least 2;
      identify a slice of interest by automatically detecting a radiological sign in one of the displayed slices;
      detect a selection of a region of interest in the slice of interest; and
      display additional slices out of every N slices of the reconstructed set of individual tomosynthesis slices to display regions of slices of the set of tomosynthesis slices corresponding to the selected region of interest on the display monitor.

2. The method according to claim 1, comprising selecting a region of interest in the slice of interest manually via an interaction device, semi-automatically via a device or automatically.

3. The method according to claim 1, wherein displaying regions of slices of the set corresponding to the selected region of interest on the display monitor utilizes slices in the set contiguous to the slice of interest.

4. The method according to claim 1, further comprising redisplaying the at least one slice out of every N slices of the reconstructed individual tomosynthesis slices, the redisplay being initiated manually with an interaction device, or semi-automatically via a device, or automatically.

5. The method according to claim 1, further comprising:
   compressing at least part of the set of reconstructed individual tomosynthesis slices using a data compressor which generates compressed data; and
   decompressing the compressed data;
      wherein the compressing at least part of the set of slices comprises implementing a lossless or lossy compression method.

6. The method according to claim 1, wherein N is equal to 2.

7. The method according to claim 1, wherein the second display increment corresponds to the consecutive display of all the slices of at least part of the set.

8. A system to process tomosynthesis slices, the system comprising:
   a machine configured to acquire image data of an object of interest comprising
      an X-ray emitter,
      a detector and
      a calculator configured to reconstruct a set of individual tomosynthesis slices of the object from the acquired image data
   a display monitor;
   a processor in communication with the machine, the processor configured to manage a display of slices acquired from the machine on the monitor; and
   a selection device configured to select a region of interest in a slice of interest;
      wherein the processor is further configured to:
         display at least one slice out of every N slices of the reconstructed set of individual tomosynthesis slices on a display monitor, where N is an integer value of at least 2;
         identify a slice of interest by automatically detecting a radiological sign in one of the displayed slices;
         detect a selection of the region of interest by the selection device in the slice of interest; and
         display additional slices out of every N slices of the reconstructed set of individual tomosynthesis slices to display regions of slices of the set of tomosynthesis slices corresponding to the selected region of interest on the display monitor.

9. The system according to claim 8, further comprising a data compressor.

* * * * *